Figure 1:
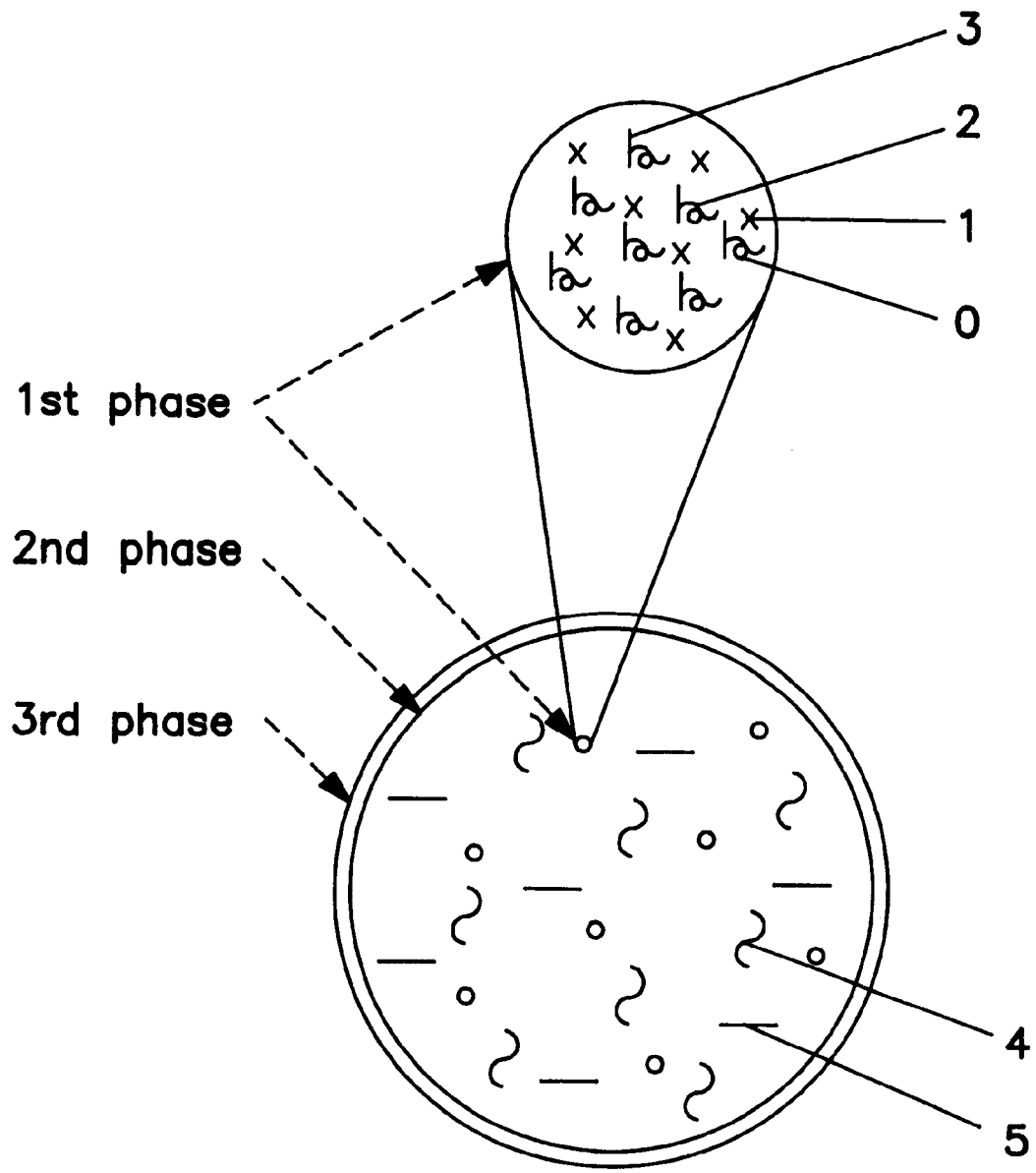

United States Patent [19]
Kerč et al.

[11] Patent Number: 6,042,847
[45] Date of Patent: Mar. 28, 2000

[54] THREE-PHASE PHARMACEUTICAL FORM WITH CONSTANT AND CONTROLLED RELEASE OF AMORPHOUS ACTIVE INGREDIENT FOR SINGLE DAILY APPLICATION

[75] Inventors: Janez Kerč; Ljubomira Barbara Rebič, both of Ljubljana; Bojan Kofler, Škofja Loka, all of Slovenia

[73] Assignee: LEK, Tovarna farmacevtskih in Kemicnih Izdelkov, d.d., Ljubljana, Slovenia

[21] Appl. No.: 08/945,984

[22] PCT Filed: May 17, 1996

[86] PCT No.: PCT/SI96/00012

§ 371 Date: Nov. 12, 1997

§ 102(e) Date: Nov. 12, 1997

[87] PCT Pub. No.: WO96/36318

PCT Pub. Date: Nov. 21, 1996

[30] Foreign Application Priority Data

May 19, 1995 [SI] Slovenia ................. P-9500173

[51] Int. Cl.$^7$ ................................................. A61K 9/24
[52] U.S. Cl. .................................................. 424/472
[58] Field of Search .................................... 424/472

[56] References Cited

U.S. PATENT DOCUMENTS

| 4,259,314 | 3/1981 | Lowey ........................... 424/19 |
| 4,327,725 | 5/1982 | Cortese et al. ................. 128/260 |
| 4,389,393 | 6/1983 | Schor et al. .................... 424/19 |

(List continued on next page.)

FOREIGN PATENT DOCUMENTS

| 0 596 203 A1 | 5/1994 | European Pat. Off. . |
| WO 87/00044 | 1/1987 | WIPO . |
| WO 91/17743 | 11/1991 | WIPO . |

OTHER PUBLICATIONS

Shaikh, N.A. et al., "Evaluation of Ethylcellulose as a Matrix for Prolonged Release Formulations. I. Water Soluble Drugs: Acetaminophen and Theophylline", *Drug Development and Industrial Pharmacy*, 13(8), 1345–1369 (1987).

*Primary Examiner*—Michael A. Williamson
*Attorney, Agent, or Firm*—Pollock, Vande Sande & Amernick

[57] ABSTRACT

Described is a novel three-phase pharmaceutical form with constant and controlled release of an amorphous active ingredient stabilized with polymers for a single daily peroral application, which is especially suitable for active ingredients existing in amorphous form or in one or more polymorphous forms, which exhibit poor solubility in crystal form depending on the polymorphous form, particle size and the specific surface area of the active ingredient. The active ingredient can be used in its amorphous or any polymorphous form, which in the process of the preparation of the three-phase pharmaceutical form according to the invention is converted into the amorphous form. The three-phase pharmaceutical form with constant and controlled release of an amorphous active ingredient for a single daily peroral application contains a core consisting of a first and a second phase and a coating representing the third phase. In the first phase the three-phase pharmaceutical form contains an amorphous active ingredient, the water-soluble polymer polyvinylpyrrolidone and a cellulose ether as carriers of the amorphous active ingredient and simultaneously as inhibitors of its crystallization, a surfactant that improves the solubility of the active ingredient and promotes the absorption of the amorphous active ingredient from gastrointestinal tract, in the second phase it contains a cellulose ether and a mixture of mono-, di- and triglycerides as sustained release agents and the third phase is represented by a poorly soluble or gastro-resistant film coating, which in the first few hours after the application controls the release of the active ingredient and can consist of an ester of hydroxypropylmethylcellulose with phthalic anhydride or of a copolymerizate based on methacrylic acid and ethyl acrylate. Described is also a process for the preparation of this pharmaceutical form.

63 Claims, 1 Drawing Sheet

U.S. PATENT DOCUMENTS

| | | | |
|---|---|---|---|
| 4,412,986 | 11/1983 | Kawata et al. | 424/80 |
| 4,612,008 | 9/1986 | Wong et al. | 604/892 |
| 4,765,989 | 8/1988 | Wong et al. | 424/473 |
| 4,783,337 | 11/1988 | Wong et al. | 424/468 |
| 4,792,452 | 12/1988 | Howard et al. | 424/475 |
| 4,871,548 | 10/1989 | Edgren et al. | 424/488 |
| 4,892,741 | 1/1990 | Ohm et al. | 424/479 |
| 5,009,895 | 4/1991 | Lui | 424/465 |
| 5,015,479 | 5/1991 | Mulligan et al. | 44/457 |
| 5,264,446 | 11/1993 | Hegasy et al. | 514/356 | ns
THREE-PHASE PHARMACEUTICAL FORM WITH CONSTANT AND CONTROLLED RELEASE OF AMORPHOUS ACTIVE INGREDIENT FOR SINGLE DAILY APPLICATION

TECHNICAL FIELD OF THE INVENTION

The invention belongs to the field of pharmaceutical industry and relates to a novel medicinal preparation with prolonged action for peroral application (sustained release tablets) based on a combination of an amorphous active ingredient, water-soluble polymer polyvinylpyrrolidone, cellulose ethers and a mixture of mono-, di- and triglycerides, an ester of hydroxypropylmethylcellulose with phthalic anhydride or a copolymer based on methacrylic acid and ethyl acrylate.

Particularly, the invention relates to a novel three-phase pharmaceutical form with a constant and controlled release of an amorphous active ingredient stabilized with polymers for a single daily peroral application such as tablets and capsules. A three-phase pharmaceutical form with constant and controlled release of an amorphous active ingredient for a single daily peroral application is especially suitable for active ingredients existing in amorphous form or in one or more polymorphous forms, which exhibit poor solubility in crystal form depending on the polymorphous form, particle size and specific surface area of the active ingredient. The active ingredient can be used in amorphous or any polymorphous form which is converted into the amorphous form during the manufacturing process of the three-phase pharmaceutical form of the invention. The three-phase pharmaceutical form with constant and controlled release of the amorphous active ingredient for a single daily peroral application contains a core consisting of a first and a second phase and a coating representing the third phase. The three-phase pharmaceutical form contains as the first phase an amorphous active ingredient, the water-soluble polymer polyvinylpyrrolidone and a cellulose ether as carriers of the amorphous active ingredient and simultaneously as inhibitors of crystallization of the amorphous active ingredient as well as a surfactant improving the solubility of the active ingredient and promoting the absorption of the amorphous active ingredient from the gastrointestinal tract; as the second phase it contains sustained-release agents such as cellulose ether and a mixture of mono-, di- and triglycerides, and the third phase is represented by a poorly soluble or gastro-resistant film coating, which in the first few hours after the application controls the release of the active ingredient and can consist of an ester of hydroxypropylmethylcellulose with phthalic anhydride or of a copolymerizate based on methacrylic acid and ethyl acrylate.

TECHNICAL PROBLEM

There exists a constant need to develop pharmaceutical forms in which solubility and dissolution rate of the active ingredient will be independent of its polymorphous form, crystallinity, particle size and specific surface area. Hitherto known pharmaceutical forms with prolonged release of the active ingredient containing a crystalline active ingredient in the pharmaceutical form have the essential disadvantage that, due to the presence of the crystalline active ingredient in several polymorphous modifications, the release rate of the active ingredient depends on the polymorphous modification, the crystal size and thus on the specific surface area of the active ingredient. The dissolution rate of a crystalline substance is not constant and it changes depending on various shapes and size distribution of the crystals of the active ingredient.

PRIOR ART

The use of cellulose ethers of various viscosities and molecular weights in the function of controlling the release rate has been known for a long time. In U.S. Pat. No. 4,259,314 there is described a method for the preparation of a dry pharmaceutical preparation with controlled and sustained release, which is provided by a mixture of hydroxypropylmethylcellulose and hydroxypropylcellulose together with a hygroscopic active ingredient.

N. A. Shaikh, S. E. Abidi and L. H. Block (Drug Development and Industrial Pharmacy, 13 (8), 1345–1369 (1987)) studied the influence of the concentration of ethylcellulose in a pharmaceutical preparation on the release rate of the active ingredient (e.g. acetaminophen, theophyline). It was found that the higher is the viscosity of ethylcellulose the lower is the release rate of the active ingredient from a solid dispersion.

In U.S. Pat. No. 4,389,393 there is described a carrier basis for active ingredients consisting of one or more hydroxypropylmethylcelluloses with various contents of methoxy or hydroxypropoxy groups and various average molecular weights, which combination gives a pharmaceutical preparation with sustained release.

In U.S. Pat. No. 4,792,452 there is described a pharmaceutical form with a controlled release of the active ingredient (selected from the group of calcium antagonists) independently of the pH-value of the environment, which contains up to 45 wt. % of a polymer dependent of the pH value, which is an alginic acid salt e.g. sodium alginate, and a gelatinizing agent independent of the pH-value such as hydroxypropylmethylcellulose.

In WO 87/00044 there is described the use of bimodal hydroxypropylmethylcellulose in a carrier basis which together with the active ingredient gives a bimodal profile of the release of the active ingredient.

In WO 91/17743 a pharmaceutical preparation for a slow release of granules containing low and high viscous ethylcellulose is described.

In U.S. Pat. No. 5,009,895 there is described a carrier basis in combination with an active ingredient (e.g. ibuprofen or its salt) that is formed and compressed in a solid pharmaceutical form with a sustained release of the active ingredient. The carrier basis contains two hydroxypropylmethylcelluloses of different viscosities in such a ratio that the release rate of the active ingredient is of zero order. In the pharmaceutical form there is also present polyvinylpyrrolidone (Povidon USP) acting as a binding agent.

In EP-A-596 203 there is described a pharmaceutical form containing solid particles, which is prepared by mixing an active ingredient (e.g. nifedipine) with a water-soluble melt consisting of two sorts of polymers with different viscosities (polymer A with a viscosity from 1000 to 120000 mPa.s, polymer B with a viscosity from 1 to 500 mPa.s) as a carrier.

A dosage form containing cellulose ethers with various molecular weights is described also in U.S. Pat. No. 4,871,548.

In U.S. Pat. No. 5,015,479, there is described a pharmaceutical preparation for a single daily application in the form of an adsorbate containing amorphous dihydropyridine (such as felodipine, nicardipine, nifedipine) and polyvinylpyrrolidone with average molecular weight above 55000 g/mol, whose role is to change the dissolution rate of dihydropyridine from cross-linked polyvinylpyrrolidone and to prevent the crystallization of dihydropyridine. Dihydropyridine and polyvinylpyrrolidone are adsorbed on cross-linked polyvinylpyrrolidone and mixed with a polymer which gelatinates in the presence of water (e.g. polyvinyl alcohol, polyvinylpyrrolidone, hydroxyethylcellulose, sodium carboxymethylcellulose etc.). The quantity and the ratio between water-soluble and water-insoluble polymers with regard to the viscosity of polyvinylpyrrolidone provides the desired sustained release.

DESCRIPTION OF THE SOLUTION TO THE TECHNICAL PROBLEM WITH EXAMPLES

The aim of the invention is to prepare a novel pharmaceutical preparation for a single daily peroral application, wherefrom the amorphous active ingredient is released with a constant and controlled rate of zero order and wherein the solubility and dissolution rate of the active ingredient are independent of its polymorphous form, crystallinity, particle size and specific surface area. This aim was achieved by the preparation of a three-phase pharmaceutical form according to the invention, wherein the active ingredient in amorphous form is stabilized by a mixture of polymers comprising water-soluble polymer polyvinylpyrrolidone and cellulose ethers of various viscosities. The release of the amorphous active ingredient from the three-phase pharmaceutical form is determined by the mixture of water-soluble polymer polyvinylpyrrolidone, a surfactant, cellulose ethers of various viscosities, a mixture of mono-, di- and triglycerides and, additionally, the release is also influenced by a film coating consisting of an ester of hydroxypropylmethylcellulose with phthalic anhydride or of a copolymerizate based on methacrylic acid and ethyl acrylate. The amorphous active ingredient stabilized with polymers is dispersed in a mixture of these polymers at the molecular level and has therefore always the same particle size, the same specific surface area and, consequently, a constant release rate in a 24-hour interval. For various active ingredients the pharmaceutical preparation of the invention has such bioavailability as determined by clinical tests that is comparable with known commercial preparations based on completely different principles of releasing the active ingredient (e.g. the principle of osmosis in OROS-system described in U.S. Pat. Nos. 4,327,725, 4,612,008, 4,765,989 and 4,783,337, suitable for various active ingredients such as nifedipine).

The main aim of the invention refers to a novel three-phase pharmaceutical form with constant and controlled release of an amorphous active ingredient for a single daily peroral application, containing a core consisting of a first and a second phase containing an amorphous active ingredient, the water-soluble polymer polyvinylpyrrolidone, a surfactant, cellulose ethers and a mixture of mono-, di- and triglycerides, and a coating representing the third phase and consisting of an ester of hydroxypropylmethylcellulose with phthalic anhydride or a copolymerizate based on methacrylic acid and ethyl acrylate.

A schematic presentation of the three-phase pharmaceutical form is iven in FIG. 1. There in the first phase of the three-phase pharmaceutical form contains an amorphous active ingredient (0), a surfactant (1), the water-soluble polymer polyvinylpyrrolidone (2) and a cellulose ether (3). The second phase of the three-phase pharmaceutical form contains a cellulose ether (4) of the second phase and a mixture (5) of mono-, di- and triglycerides. The third phase is represented by a film coating consisting of an ester of hydroxypropylmethylcellulose with phthalic anhydride or a copolymerizate based on methacrylic acid and ethyl acrylate.

The first phase of the three-phase pharmaceutical form with constant and controlled release of an amorphous active ingredient for a single daily peroral application contains an amor phous active ingredient, the water-soluble polymer polyvinylpyrrolidone, a surfactant and a cellulose ether.

In the novel three-phase pharmaceutical form with constant and controlled release of an amorphous active ingredient for a single daily peroral application according to the invention, various active ingredients in amounts ranging from 0,05 mg to 300 mg can be used, which exist in amorphous form or in one or more polymorphous modifications, which have poor solubility in crystal form depending on its polymorphous form, particle size and specific surface area. As active ingredients in the three-phase pharmaceutical form with constant and controlled release of an amorphous active ingredient for a single daily peroral application there can be used various active ingredients acting as analgesics, anticonvulsants, antiparkinsonian drugs, anesthetics, antibiotics, antimalarials, antihypertensives, antihistaminics, antipyretics, alpha-blockers, alpha-adrenergic agonists, bactericides, bronchodilators, beta-adrenergic stimulants, beta-adrenergic blockers, contraceptives, cardiovascular active ingredients, calcium channel inhibitors, diuretics, hypnotics, hormones, hyperglycemics, hypoglycemics, muscle relaxants and contractors, parasympathomimetics, sedatives, sympathomimetics, tranquilizers, antimigraine drugs, vitamins and many others.

The three-phase pharmaceutical form with constant and controlled release of an amorphous active ingredient for a single daily peroral application is especially useful for dihydropyridines selected from a group comprising nicardipine hydrochloride, amlodipine benzenesulfonate, nifedipine, felodipine and fenofibrate and other active ingredients poorly soluble in water.

The water-soluble polymer polyvinylpyrrolidone in the first phase of the three-phase pharmaceutical form with constant and controlled release of an amorphous active ingredient for a single daily peroral application prevents the crystallization of the amorphous active ingredient, simultaneously it is a carrier of the amorphous active ingredient and it improves the wettability and dissolving rate of the amorphous active ingredient. As the water-soluble polymer polyvinylpyrrolidone there can be used a polyvinylpyrrolidone with a K-value (relative viscosity of the compound in water solution with regard to water) ranging from 10 to 95, preferably in the range from 24 to 32, with an average molecular weight ranging from 2000 g/mol to 1100000 g/mol, preferably in the range from 25000 g/mol to 50000 g/mol. The water-soluble polymer polyvinylpyrrolidone is present in the three-phase pharmaceutical form in the range from 1 to 40 wt. %, preferably from 4 to 20 wt. %, with respect to the total weight of the three-phase pharmaceutical form.

In the first phase of the three-phase pharmaceutical form with constant and controlled release of an amorphous active ingredient for a single daily peroral application the added surfactant improves the wettability, solubility and dissolution rate, and provides a perfect absorption of the dissolved amorphous active ingredient from the gastrointestinal tract. As the surfactant there can be used ionic surfactants such as sodium lauryl sulfate or non-ionic surfactants such as various types of poloxamers (copolymers of polyoxyethylene and polyoxypropylene), natural or synthetic lecithins and esters of sorbitan and fatty acids (such as Span® (Atlas Chemie)), esters of polyoxyethylene sorbitan and fatty acids (such as Tween® (Atlas Chemie)), polyoxyethylated hydrogenated castor oil (such as Cremophor® (BASF)), polyoxyethylene stearates (such as Myrj® (Atlas Chemie)) or any other combinations of the cited surfactants. In the three-phase pharmaceutical form the surfactant is present in the range from 0.1 to 20 wt. %, preferably from 0.2 to 10 wt. % with respect to the total weight of the three-phase pharmaceutical form. For providing the wettability of the active ingredient and its absorption from the gastrointestinal tract the required weight ratio between the surfactant and the active ingredient is in the range from 0.1:100 to 10:1, preferably in the range from 0.5:100 to 3:1.

The cellulose ether in the first phase of the three-phase pharmaceutical form with constant and controlled release of an amorphous active ingredient for a single daily peroral application acts as a carrier of the amorphous active ingredient which simultaneously inhibits its crystallization. As the cellulose ether there can be used methylcellulose, ethylcellulose, hydroxyethylcellulose, propylcellulose, hydroxypropylcellulose, hydroxypropylmethylcellulose, carboxymethylcellulose, preferably hydroxyethylcellulose, hydroxypropylcellulose and hydroxypropylmethylcellulose with viscosity in the range from 3 to 1500 mPa.s, preferably in the range from 5 to 400 mPa.s and with an average molecular weight in the range from 5000 g/mol to 50000 g/mol, preferably in the range from 10000 g/mol to 30000 g/mol. As the cellulose ether hydroxypropylmethylcellulose with a content of methoxy groups ranging from 19 to 30% and with a content of hydroxypropoxy groups ranging from 4 to 12% can be used. In the first phase of the three-phase pharmaceutical form the cellulose ether is present in a quantity from 10 to 70 wt. %, preferably from 20 to 60 wt. %, with respect to the total weight of the three-phase pharmaceutical form.

For providing a stable amorphous form of the active ingredient in the novel three-phase pharmaceutical form with constant dissolution rate the required weight ratio between the water-soluble polymer polyvinylpyrrolidone and the cellulose ether in the first phase of the three-phase pharmaceutical form with constant and controlled release of the amorphous active ingredient for a single daily peroral application is in the range from 1:10 to 10:1, preferably in the range from 1:3 to 3:1.

The combination of the carriers i.e. the water-soluble polymer polyvinylpyrrolidone and the cellulose ether has a double effect and the advantage that it stabilizes the amorphous form of the active ingredient and simultaneously modifies the release of the amorphous active ingredient in such a way that it is sustained, repeatable and independent of the amorphous or polymorphous form of the active ingredient, its particle size and specific surface area.

For providing a stable amorphous form of the active ingredient with a constant dissolution rate, the required weight ratio between the amorphous active ingredient, water soluble polymer polyvinylpyrrolidone and cellulose ether in the first phase of the three-phase pharmaceutical form is in the range from 1:20:30 to 10:2:1, preferably in the range from 1:2:3 to 3:2:1.

The second phase of the three-phase pharmaceutical form with constant and controlled release of an amorphous active ingredient for a single daily peroral application contains a cellulose ether, a mixture of mono-, di- and triglycerides and other usual adjuvants useful in the preparation of solid pharmaceutical forms such as fillers, binders, swelling auxiliaries, glidants, lubricants etc. The cellulose ethers and the mixture of mono-, di- and triglycerides modify the release rate of the amorphous active ingredient in such a manner that a constant release (a release of zero order) of the amorphous active ingredient in a 24-hour interval is achieved.

In the second phase of the three-phase pharmaceutical form with constant and controlled release of an amorphous active ingredient for a single daily peroral application as cellulose ethers gelatinizing in the presence of water there can be used methylcellulose, ethylcellulose, hydroxyethylcellulose, propylcellulose, hydroxypropylcellulose, hydroxypropylmethylcellulose, carboxymethylcellulose, preferably hydroxypropylcellulose and hydroxypropylmethylcellulose with viscosity in the range from 1500 to 150000 mPa.s, preferably in the range from 4000 to 100000 mPa.s and with an average molecular weight ranging from 50000 g/mol to 300000 g/mol, preferably in the range from 80000 g/mol to 250000 g/mol. As the cellulose ether hydroxypropylmethylcellulose with a content of methoxy groups ranging from 19 to 30% and with a content of hydroxypropoxy groups ranging from 4 to 12% can be used. In the second phase of the tree-phase pharmaceutical form the cellulose ether is present in the amount from 5 to 40 wt. %, preferably from 10 to 30 wt. %, with respect to the total weight of the three-phase pharmaceutical form. The cellulose ethers in the second phase act as an agent for sustained and controlled release of the amorphous active ingredient. Thus the cellulose ethers in the first and in the second phases of the three-phase pharmaceutical form have a different function.

The mixture of mono-, di- and triglycerides acts as a glidant with a sustained release action. As the mixture of mono-, di- and triglycerides there can be used a mixture of glycerol mono-, di- and tristearate, a mixture of glycerol mono-, di- and tripalmitate, a mixture of glycerol mono-, di- and trioleate, a mixture of glycerol mono-, di- and tripalmitostearate, preferably a mixture of glycerol mono-, di- and tripalmitostearate with a weight content from 20 to 60 wt. % of triglyceride, from 25 to 65 wt. % of diglyceride, from 10 to 20 wt. % of monoglyceride and from 0 to 5 wt. % of glycerol, preferably from 35 to 45 wt. % of triglyceride, from 40 to 50 wt. % of diglyceride, from 12 to 16 wt. % of monoglyceride and from 1 to 2 wt. % of glycerol. The mixture of mono-, di- and triglycerides is present in the second phase of the three-phase pharmaceutical form in an amount from 0 to 10 wt. %, preferably from 0 to 5 wt. % with respect to the total weight of the three-phase pharmaceutical form.

For providing a constant and controlled release of zero order of the amorphous active ingredient from the three-phase pharmaceutical form with constant and controlled release of an amorphous active ingredient for a single daily peroral application the required weight ratio between the cellulose ether in the first phase and the cellulose ether in the second phase is in the range from 5:1 to 1:5, preferably in the range from 3:1 to 1:3.

In the second phase the three-phase pharmaceutical form with constant and controlled release of an amorphous active ingredient for a single daily peroral application can, beside cited ingredients, contain also other nontoxic excipients useful in pharmaceutical forms. The three-phase form can also contain one or more fillers such as lactose, starch, saccharose, glucose, microcrystalline cellulose, mannitol, sorbitol, calcium hydrogen phosphate, aluminum silicate, sodium chloride etc., one or more binders such as starch, gelatin, carboxymethylcellulose, polyvinylpyrrolidone, crosslinked polyvinylpyrrolidone, sodium alginate, microcrystalline cellulose etc., one or more disintegrants such as starch, cross-linked sodium carboxymethylcellulose, crosslinked polyvinylpyrrolidone, sodium starch glycolate etc., one or more glidants such as magnesium stearate, calcium stearate, aluminum stearate, stearic acid, palmitic acid, cetanol, stearol, polyethylene glycols of various molecular weights, talc etc., one or more lubricants such as stearic acid, calcium, magnesium or aluminum stearate, siliconized talc etc.

The third phase of the three-phase pharmaceutical form with constant and controlled release of an amorphous active ingredient for a single daily peroral application is represented by a poorly soluble or gastro-resistant film coating for additional delay in release and for adaptation to in vivo release rates of known commercial preparations.

The film coating consists of an ester of hydroxypropylmethylcellulose with phthalic anhydride with an average molecular weight ranging from 2000 g/mol to 100000 g/mol, with a content of methoxy groups from 18 to 25%, a content of hydroxypropoxy groups from 4 to 10%, a content of carboxybenzoyl groups from 20 to 35%, a viscosity in the range from 120 to 180 mPa.s; the weight ratio of the coating with respect to the core is from 2 to 10 wt. %, preferably from 3 to 7 wt. %;

or of a copolymerizate of methacrylic acid and ethyl acrylate with an average molecular weight ranging from 100000 g/mol to 300000 g/mol, a content of methacrylic groups from 40 to 50% and a viscosity in the range from 100 to 200 mPa.s; the weight ratio of the coating with respect to the core is from 2 to 15 wt. %, preferably from 3 to 10 wt. %.

In addition to the cited polymers, the third phase can also contain one or more plasticizers such as polyethylene glycols of various molecular weights, triacetine, dibutyl sebacate, triethyl citrate, cellulose ethers such as hydroxypropylcellulose, hydroxypropylmethylcellulose etc., additives such as talc, pigments such as synthetic ferric (III) oxide, synthetic ferric (III) oxide hydrate, titanium dioxide etc.

The object of the invention also relates to a process for the preparation of the three-phase pharmaceutical form with constant and controlled release of an amorphous active ingredient for a single daily peroral application, wherein as the active ingredient an amorphous or a polymorphous form of the active ingredient can be used.

In the first step of the preparation of the three-phase pharmaceutical form with constant and controlled release of an amorphous active ingredient for a single daily peroral application an active ingredient, a surfactant and the water-soluble polymer polyvinylpyrrolidone are dissolved in an organic solvent at a temperature from 30° C. to 70° C., and in a fluid bed granulator the obtained solution is sprayed onto cellulose ether in the fluid bed. As the active ingredient there can be used an amorphous form or a polymorphous form of the active ingredient which in the process of coprecipitation according to the invention is converted into an amorphous form stabilized with the water-soluble polymer polyvinylpyrrolidone and a cellulose ether. Organic solvents useful for this purpose can be selected from a group of alcohols, ketones, esters, ethers, aliphatic hydrocarbons, halogenated hydrocarbons, cycloaliphatic, aromatic, heterocyclic solvents or mixtures thereof. Typical solvents can be ethanol, methanol, isopropyl alcohol, n-butyl alcohol, acetone, diethyl ether, ethyl acetate, isopropyl acetate, methyl acetate, dichloromethane, chloroform, mixtures of these solvents such as ethanol and acetone, methanol and acetone, dichloromethane and methanol and mixtures thereof. If a polymorphous form of the active ingredient is chosen, it is in the process of the invention converted into an amorphous form which is stabilized with the water-soluble polymer polyvinylpyrrolidone and a cellulose ether. The obtained granulate is regranulated through a sieve of mesh size 0.5 mm at room temperature.

The second step of the preparation of the three-phase pharmaceutical form is conducted in such a manner that at room temperature the granulate obtained in the first step is homogeneously mixed with a cellulose ether and other usual adjuvants useful in the preparation of solid pharmaceutical forms such as lactose, polyvinylpyrrolidone, cross-linked polyvinylpyrrolidone, starch, calcium hydrogen phosphate, aluminum silicate, magnesium stearate, talc, or generally with fillers, binders, disintegrants, glidants, lubricants etc.

The components are compressed into tablets by means of known tableting machines. Thus it is possible to prepare tablets with constant and controlled release of an amorphous active ingredient in a relatively simple and economical way.

In the third step of the preparation of the three-phase pharmaceutical form by means of a film coating an additional delay of the release of the amorphous active ingredient from the three-phase pharmaceutical form and a comparable in vivo release rates of the active ingredient with regard to the release rates of the active ingredient from known commercial preparations are achieved. The film coating can consist of a copolymerizate of methacrylic acid and ethyl acrylate or of an ester of hydroxypropylmethylcellulose with phthalic anhydride.

The film coating is prepared by dissolving the polymers in an organic solvent, in mixtures of organic solvents or in mixtures thereof with water. As organic solvents ethanol, methanol, isopropanol or acetone can be used. To the polymer solution plasticizers such as polyethylene glycols of various molecular weights, triacetine, triethyl citrate, dibutyl sebacate etc. are added. In a core coating pan the coating is sprayed onto the cores, whereupon by a colour coating they are protected from the influence of the light. In the film coating for the protection from light cellulose ethers such as hydroxypropylmethylcellulose, hydroxypropylcellulose etc., plasticizers such as polyethylene glycols of various molecular weights, triacetine, triethyl citrate, dibutyl sebacate etc., pigments such as synthetic ferric (III) oxide, synthetic ferric (III) oxide hydrate, titanium dioxide etc. are used.

A combination of the amorphous form of an active ingredient, the water-soluble polymer polyvinylpyrrolidone, a surfactant, cellulose ethers and a mixture of mono-, di- and triglycerides, prepared in a certain ratio between the single components of the system according to the process of the invention, which is simple and technologically as well as economically acceptable, has hitherto not been described in the literature. The granulate of an amorphous active ingredient, the water-soluble polymer polyvinylpyrrolidone, cellulose ethers and other ingredients suitable for the preparation of solid pharmaceutical forms has good compressibility, so prepared tablets are firm, have low brittleness and make possible a constant controlled release of the amorphous active ingredient.

The invention is illustrated, but in no way limited by the following examples.

EXAMPLE 1

The core of a tablet consisting of the first and the second phase of the three-phase pharmaceutical form containing 60 mg of niferdipine

| Composition of one tablet: | |
|---|---|
| Nifedipine | 60.0 mg |
| Polyvinylpyrrolidone K25 | 150.0 mg |
| Sodium lauryl sulfate | 4.8 mg |
| Hydroxypropylmethylcellulose 50 mPa.s | 203.8 mg |
| Hydroxypropylmethylcellulose 100000 mPa.s | 99.4 mg |
| Ludipress | 50.0 mg |
| Talc | 6.0 mg |
| Magnesium stearate | 6.0 mg |

A series of 2500 tablets was prepared according to the following process:

Crystalline nifedipine (150.0 g), sodium lauryl sulfate (12.0 g) and polyvinylpyrrolidone K25 (375.0 g) (Kollidon 25 BASF; Plasdone K-25 ISP GAF) were dissolved in ethanol (1830.0 g) under intensive stirring at a temperature from 55° C. to 60° C. The formed solution (2367 g) heated to 55° C. to 60° C. was in a fluid bed at an inlet air temperature from 70° C. to 80° C. sprayed onto hydroxypropylmethylcellulose with a viscosity of 50 mPa.s (Methocel F50 Premium, Dow Chemicals) and with an average molecular weight of 19000 g/mol. The so prepared granulate (1046 g) was dried in a fluid bed and regranulated through a sieve with mesh size 0.5 mm. To the granulate there were added hydroxypropylmethylcellulose (248.5 g) with a viscosity of 100000 mPa.s (Methocel K100M, Premium, Dow Chemicals) and an average molecular weight of 215000 g/mol, Ludipress (125.0 g) (93.4 wt. % of lactose monohydrate +3.2 wt. % of polyvinylpyrrolidone K30 (Kollidon 30) +3.4 wt. % of cross-linked polyvinylpyrrolidone (Kollidon CL, BASF Germany)), talc (12.0 g) and magnesium stearate (12.0 g) and they were homogeneously blended at room temperature. The so prepared granulate with amorphous nifedipine was tableted in a usual tableting machine so that tablets with a weight of 580 mg were obtained.

Dissolution Test (release rate)

Apparatus: apparatus 2 (USP 23), 100 RPM

Medium: 0.10% Tween 80 (polyoxyethylene(20)sorbitan monooleate) in artificial gastric juice pH 1.2, 4000 ml Temperature: 37° C.

Quantitative analysis: UV spectrophotometry, 340 nm

TABLE 1

Percentage of released nifedipine vs. dissolution time

| Dissolution time (hours) | Percentage of released nifedipine |
|---|---|
| 1 | 2.6 |
| 2 | 6.4 |
| 4 | 14.6 |
| 6 | 21.8 |
| 8 | 31.1 |
| 12 | 50.0 |
| 14 | 58.3 |
| 16 | 67.0 |
| 18 | 75.5 |
| 20 | 85.7 |
| 22 | 97.2 |
| 24 | 100.7 |

From the above table it is evident that in a 24-hour interval the active ingredient was released from the formulation with a constant rate.

EXAMPLE 2

A tablet core consisting of the first and the second phase of the tree-phase pharmaceutical form containing 60 mg of nifedipine

| Composition of one tablet | |
|---|---|
| Nifedipine | 60.0 mg |
| Polyvinylpyrrolidone K25 | 150.0 mg |
| Sodium lauryl sulfate | 4.8 mg |
| Hydroxypropylmethylcellulose 50 mPa.s | 203.8 mg |
| Hydroxypropylmethylcellulose 15000 mPa.s | 149.4 mg |
| Ludipress | 50.0 mg |
| Talc | 6.0 mg |
| Magnesium stearate | 6.0 mg |

Tablets were prepared according to the same process as in Example 1, only that the hydroxypropylmethylcellulose with a viscosity of 100000 mPa.s (Methocel K100M Premium, Dow Chemicals) was replaced by hydroxypropylmethylcellulose with a viscosity of 15000 mPa.s and an average molecular weight of 125000 g/mol (Methocel K15MP, Dow Chemicals). Tablets with a weight of 630 mg were obtained.

Dissolution Test (release rate)

Apparatus: apparatus 2 (USP 23), 100 RPM

Medium: 0–2 hours: artificial gastric juice, 4000 ml 2–24 hours: artificial intestinal juice, 4000 ml Temperature: 37° C.

Quantitative analysis: UV spectrophotometry, 340 nm

TABLE 2

Percentage of released nifedipine vs. dissolution time

| Dissolution time (hours) | Percentage of released nifedipine |
|---|---|
| 1 | 4.2 |
| 2 | 9.1 |
| 4 | 18.1 |
| 6 | 26.2 |
| 8 | 37.3 |
| 12 | 55.1 |
| 14 | 65.6 |
| 16 | 81.7 |
| 18 | 95.5 |
| 24 | 99.8 |

From the above table it is evident that in a 24-hour interval the active ingredient was released from the formulation with a constant rate.

EXAMPLE 3

Tablet core consisting of the first and the second phase of the three phase pharmaceutical form containing 60 mg of nifedipine

| Composition of one tablet | |
|---|---|
| Nifedipine | 60.0 mg |
| Polyvinylpyrrolidone | 150.0 mg |
| Sodium lauryl sulfate | 4.8 mg |
| Hydroxypropylmethylcellulose 50 mPa.s | 203.8 mg |
| Hydroxypropylmethylcellulose 4000 mPa.s | 179.4 mg |
| Precirol ATO 5 | 10.0 mg |
| Ludipress | 50.0 mg |
| Talc | 6.0 mg |
| Magnesium stearate | 6.0 mg |

Tablets were prepared according to the same process as in Example 1, only that the hydroxypropylmethylcellulose with a viscosity of 100000 mPa.s (Methocel K100M Premium, Dow Chemicals) was replaced by hydroxypropylmethylcellulose with a viscosity of 4000 mPa.s and an average molecular weight of 90000 g/mol (Methocel K4M, Dow Chemicals) and Precirol ATO 5 (a mixture of mono-, di- and triglycerides: 14% of palmitostearin monoglyceride, 45% of palmitostearin diglyceride, 40% of palmitostearin triglyceride, Gattefosse). Tablets with a weight of 670 mg were obtained.

Dissolution Test (release rate)

Apparatus: apparatus 2 (USP 23), 100 RPM

Medium: 0.1% Tween 80 (polyoxyethylene(20)sorbitan monooleate) in artifical gastric juice pH 1.2, 4000 ml Temperature: 37° C.

Quantitative analysis: UV spectrophotometry, 340 nm

TABLE 3

Percentage of released nifedipine vs. dissolution time

| Dissolution time (hours) | Percentage of released nifedipine |
|---|---|
| 1 | 4.4 |
| 2 | 8.3 |
| 4 | 14.4 |
| 6 | 22.6 |
| 8 | 29.5 |
| 12 | 46.0 |
| 14 | 55.5 |
| 16 | 86.8 |
| 24 | 101.9 |

From the above table it is evident that in a 24-hour interval the active ingredient was released from the formulation with a constant rate.

EXAMPLE 4

A three-phase pharmaceutical form—a tablet with constant and controlled release containing 60 mg of nifedipine Cores with the same composition as in Example 1 were prepared according to the process described in Example 1. For the preparation of the film coating for 1000 tablets the following ingredients were needed:

| | |
|---|---|
| Hydroxypropyl methylcellulose phthalate | 40.00 g |
| Triethyl citrate | 4.00 g |
| Hydroxypropylmethylcellulose | 4.50 g |
| Hydroxypropylcellulose | 4.50 g |
| Talc | 0.75 g |
| Titanium dioxide | 2.90 g |
| Synthetic ferric (III) oxide hydrate | 0.85 g |
| Polyethylene glycol 400 | 1.50 g |
| Carnauba wax | 0.48 g |

The ester of hydroxypropylmethylcellulose with phthalic anhydride (40 g) (HPMCP, Shin Etsu Chemical Co., Tokyo) and triethyl citrate (4.0 g) were dissolved under stirring in a mixture of ethanol (284.8 g) and water (71.2 g) at 30° C. The solution was sprayed onto tablets so that a film coating in a weight ratio of 7.5 wt. % with regard to the core was obtained.

After drying (20 hours at 35° C.) the tablets were also coated with a colour film coating consisting of hydroxypropylmethylcellulose (4.5 g) (Pharmacoat 606, Shin Etsu Chemical Co., Tokyo) with a viscosity of 6 mPa.s and hydroxypropylcellulose (4.5 g) (Klucel EF, Hercules, Wirlington) with an average molecular weight of 60000 g/mol and a viscosity of 5 to 10 mPa.s, both dispersed in ethanol (89.5 g) and water (38.3 g), and there were added talc (0.7 g), titanium dioxide (2.9 g), synthetic yellow ferric (III) oxide hydrate 80.8 G) (Sicopharm® Gelb 10, BASF) and polyethylene glycol (1.5 g) with a molecular weight of 400 g/mol (Polyglycol 400, Hoechst). The colour film coating represented 2.5 wt. % with regard to the cores. Tablets with colour coating were also polished with carnauba wax (0.5 g) (Carnauba Wachs 2442 P 100, Kahl, Germany). A three-phase pharmaceutical form—tablets with a weight of 639 mg—was obtained.

Dissolution Test (release rate)

Apparatus 1 (USP 23), 100 RPM

Medium: 0.2 houres: artificial gastric juice pH 1.2, 1000 ml 2–24 hours: 1% sodium lauryl sulfate in artificial intestinal juice, pH 6.9, 4000 ml Temperature: 37° C.

Quantitative analysis: UV spectrophotometry, 340 nm

TABLE 4

Percentage of released nifedipine vs. dissolution time

| Dissolution time (hours) | Percentage of released nifedipine |
|---|---|
| 2 | 1.3 |
| 4 | 10.7 |
| 6 | 20.8 |
| 8 | 30.3 |
| 12 | 51.2 |
| 18 | 81.8 |
| 20 | 90.2 |
| 22 | 97.6 |
| 24 | 101.4 |

Fron the above table it is evident that in a 24-hour interval the active ingredient was released from the three-phase formulation with a constant rate.

Comparative Bioequivalency Study

A comparative bioequivalency study of the pharmaceutical preparation according to the invention having the composition described in Example 4 (Nifedipine 60 mg sustained release tablets—designation N) and of the commercial preparation (Nifedipine 60 mg sustained release tablets—mark P) was performed.

The study was run as a double blank trial with 11 male volunteers aged from 24 to 36 years (average age 28.6 years). 24 hours before each drug application and during the trial volunteers were not allowed to consume any alcohol, coffee or chocolate. One night before the trial the volunteers were not allowed to eat. They took the tablet with 200 ml of water. After two hours they were given 200 ml of a fruit juice, 4 hours after the application they were given a standardized lunch, 10 hours after the application they were given a standardized supper and 14 hours after the application they were given a light snack. After lunch the consumption of liquids was not limited.

In certain time intervals after the application blood samples were taken and by means of high performance liquid chromatography (HPLC) plasma concentrations of the active ingredient were determined.

TABLE 5

Average plasma concentrations of nifedipine vs. time after consumption of the tablet

| Time after consumption | Plasma concentrations of nifedipine (ng/ml) | |
|---|---|---|
| (hours) | N | P |
| 1 | 1 | 1 |
| 4 | 15 | 20 |
| 6 | 22 | 18 |
| 12 | 28 | 29 |
| 18 | 25 | 24 |
| 24 | 27 | 28 |
| 30 | 23 | 23 |
| 48 | 6 | 6 |

From the above table it is evident that the plasma concentrations had values appropriate for a sustained release formulation. The pharmacokinetic parameters of both compared preparations (Nifedipine 60 mg sustained release tablets—designation N) and commercial preparation (Nifedipine 60 mg sustained release tablets—designation P) statistically did not differ significantly from each other.

EXAMPLE 5

A three-phase pharmaceutical form—a tablet with constant and controlled release containing 60 mg of nifedipine Cores with the same composition as in Example 1 were prepared according to the process described in Example 1. For the preparation of a film coating for 1000 tablets the following ingredients were needed:

| Eudragit L100-55 | 18.60 g |
|---|---|
| Polyethylene glycol 6000 | 3.12 g |
| Talc | 4.28 g |
| Hydroxypropylmethylcellulose | 4.50 g |
| Hydroxypropylcellulose | 4.50 g |
| Polyethylene glycol 400 | 1.50 g |
| Talc | 0.75 g |
| Titanium dioxide | 2.90 g |
| Synthetic ferric (III) oxide hydrate | 0.85 g |
| Carnauba wax | 0.48 g |

The copolymerizate (18.6 g) of methacrylic acid and ethyl acrylate (Eudragit L100-55, Röhm Pharma) was dissolved in a mixture of ethanol (143.6 g) and water (89.3 g) and there were added a solution of polyethylene glycol with a molecular weight of 6000 g/mol (Polyglycol 6000, Hoechst) (3.1 g) in water (6.4 g) and talc (4.3 g).

The so prepared dispersion was sprayed onto cores so that the weight of the film coating was 26.0 mg per one tablet i.e. 4.5 wt. % with respect to the core. Then the tablets were dried for 20 hours at a temperature of 35° C. A colour coating was applied in the same manner as described in Example 4. A three-phase pharmaceutical form—tablets with a weight of 621 mg—was obtained.

Dissolution Test (release rate)

Apparatus: apparatus 1 (USP 23), 100 RPM

Medium: 0–2 hourss: artificial gastric juice pH 1.2, 1000 ml 2–24 hours: 1% sodium lauryl sulfate in artificial intestinal juice pH 6.9, 400 ml Temperature: 37° C.

Quantitative analysis: UV spectrophotometry, 340 nm

TABLE 6

Percentage of released nifedipine vs. dissolution time

| Dissolution time (hours) | Percentage of released nifedipine |
|---|---|
| 2 | 1.0 |
| 4 | 10.7 |
| 6 | 21.0 |
| 8 | 29.9 |
| 12 | 52.3 |
| 18 | 87.2 |
| 20 | 95.1 |
| 24 | 101.8 |

From the above table it is evident that in a 24-hour interval the active ingredient was released from the three-phase formulation with a constant rate.

EXAMPLE 6

Three-phase pharmaceutical form—a tablet with constant and controlled release containing 30 mg of nifedipine

| Composition of one tablet | |
|---|---|
| CORE: | |
| Nifedipine | 30.0 mg |
| Polyvinylpyrrolidone K30 | 75.0 mg |
| Sodium lauryl sulfate | 2.4 mg |
| Hydroxypropylmethylcellulose 50 mPa.s | 101.9 mg |
| Hydroxypropylmethylcellulose 100000 mPa.s | 83.9 mg |
| Ludipress | 70.0 mg |
| Talc | 6.0 mg |
| Magnesium stearate | 0.8 mg |
| FILM COATING: | |
| Hydroxypropyl methylcellulose phthalate | 18.2 mg |
| Triethyl citrate | 1.8 mg |
| Hydroxypropymethylcellulose | 3.0 mg |
| Hydroxypropylcellulose | 3.0 mg |
| Talc | 0.5 mg |
| Titanium dioxide | 1.9 mg |
| Synthetic ferric (III) oxide hydrate | 0.6 mg |
| Polyethylene glycol 400 | 1.0 mg |
| Carnauba wax | 0.1 mg |

The cores were prepared according to the same process as in Example 1 and the film coating was prepared according to the same process as in Example 4. A three-phase pharmaceutical form—tablets with a weight of 400 mg—was obtained.

Dissolution Test (release rate)

Apparatus: apparatus 2 (USP 23), 100 RPM

Medium: 0–2 hours: 1.3 % sodium lauryl sulfate in 0.1 M HCl, 750 ml 2–24 hours: 1% sodium lauryl sulfate in phosphate buffer, pH =6.8, 1000 ml Temperature: 37° C.

Quantitative analysis: UV spectrophotometry, 340 nm

TABLE 7

Percentage of released nifedipine vs. dissolution time

| Dissolution time (hours) | Percentage of released nifedipine |
|---|---|
| 2 | 3.6 |
| 4 | 14.4 |
| 6 | 27.1 |
| 8 | 38.9 |
| 12 | 59.1 |
| 18 | 88.4 |
| 24 | 102.8 |

From the above table it is evident that in a 24-hour interval the active ingredient was released from the three-phase pharmaceutical form with a constant rate.

EXAMPLE 7

A three-phase pharmaceutical form—a tablet with constant and controlled release containing 90 mg of nifedipine

| Composition of one tablet | |
|---|---|
| CORE: | |
| Nifedipine | 90.0 mg |
| Polyvinylpyrrolidone K25 | 225.0 mg |
| Sodium lauryl sulfate | 7.2 mg |
| Hydroxypropylmethylcellulose 50 mPa.s | 226.6 mg |
| Hydroxypropylmethylcellulose 100000 mPa.s | 115.2 mg |
| Ludipress | 80.0 mg |
| Talc | 8.0 mg |
| Magnesium stearate | 8.0 mg |
| FILM COATING: | |
| Hydroxypropyl methylcellulose phthalate | 51.8 mg |
| Triethyl citrate | 5.2 mg |
| Hydroxypropylmethylcellulose | 6.0 mg |
| Hydroxypropylcellulose | 6.0 mg |
| Talc | 1.0 mg |
| Titanium dioxide | 3.9 mg |
| Syntbetic ferric (III) oxide hydrate | 1.1 mg |
| Polyethylene glycol 400 | 2.0 mg |
| Carnauba wax | 0.6 mg |

The cores were prepared according to the same process as in Example 1 and the film coating was prepared according to the same process as in Example 4. A three-phase pharmaceutical form—tablets with a weight of 837 mg—was obtained.

Dissolution Test (release rate)

Apparatus: apparatus 2 (USP 23), 100 RPM

Medium: 0.1% Tween 80 (polyoxyethylene(20)sorbitan monooleate) in artificial gastric juice pH 1.2, 4000 ml Temperature: 37° C.

Quantitative analysis: UV spectrophotometry, 340 nm;

TABLE 8

Percentage of released nifedipine vs. dissolution time

| Dissolution time (hours) | Percentage of released nifedipine |
|---|---|
| 2 | 3.2 |
| 4 | 13.2 |
| 8 | 30.1 |
| 12 | 49.3 |
| 16 | 62.0 |
| 20 | 84.7 |
| 24 | 99.9 |

From the above table it is evident that in a 24-hour interval the active ingredient was released from the three-phase pharmaceutical form with a constant rate.

EXAMPLE 8

A three-phase pharmaceutical form—a tablet with constant and controlled release containing 40 mg of nicardipine hydrochloride

| Composition of one tablet | |
|---|---|
| Nicardipine hydrochloride | 40.0 mg |
| Polyvinylpyrrolidone K25 | 25.0 mg |
| Sodium lauryl sulfate | 2.0 mg |
| Hydroxypropylmethylcellulose 50 mPa.s | 160.4 mg |
| Hydroxypropylmethylcellulose 4000 mPa.s | 142.4 mg |
| Precirol ATO 5 | 2.5 mg |
| Hydroxypropylcellulose | 20.0 mg |
| Microcrystalline cellulose | 53.4 mg |
| Talc | 3.0 mg |
| Stearic acid | 1.3 mg |

The cores were prepared according to the same process as in Example 1 and the film coating was prepared according to the same process as in Example 4. A three-phase pharmaceutical form—tablets with a weight of 484 mg—was obtained.

Dissolution Test (release rate)

Apparatus: apparatus 2 (USP 23), 100 RPM

Medium: 0.1% Tween 80 (polyoxyethylene(20)sorbitan monooleate) in artificial gastric juice pH 1.2, 4000 ml Temperature: 37° C.

Quantitative analysis: UV spectrophotometry, 358 nm

TABLE 9

Percentage of released nicardipine hydrochloride vs. dissolution time

| Dissolution time (hours) | Percentage of released nifedipine |
|---|---|
| 2 | 3.4 |
| 4 | 13.2 |
| 6 | 21.8 |
| 8 | 30.2 |
| 12 | 52.0 |
| 14 | 58.3 |
| 16 | 67.0 |
| 18 | 78.5 |

TABLE 9-continued

Percentage of released nicardipine hydrochloride vs. dissolution time

| Dissolution time (hours) | Percentage of released nifedipine |
|---|---|
| 20 | 87.7 |
| 22 | 96.2 |
| 24 | 100.8 |

From the above table it is evident that in a 24-hour interval the active ingredient was released from the three-phase pharmaceutical form with a constant rate.

We claim:

1. A three-phase pharmaceutical form with constant and controlled release of amorphous active ingredient for a single daily peroral application characterized in that it contains a core consisting of a first and a second phase wherein the first phase contains a mixture of an amorphous active ingredient in an amount from 0.05 mg to 300 mg, a water-soluble polymer polyvinylpyrrolidone in the range from 1 to 40 wt. % with respect to the total weight of the pharmaceutical form a surfactant in the ran(c from 0.1 to 20 wt % with respect to the total weight of the pharmaceutical form and a cellulose ether in the range from 10 to 70 wt % with respect to the total weight of the pharmaceutical form, said first phase being homogeneously mixed with the second phase containing a cellulose ether in the range from 5 to 40 wt % with respect to the total weight of the pharmaceutical form, a mixture of mono-, di- and triglycerides in the range flow 0 to 10 wt % with respect to the total weight of the pharmaceutical form and usual adjuvants;

wherein the weight ratio between the water soluble polymer polyvinylpyrrolidone and the cellulose ether in the first phase is in the range from 1:10 to 10:1, the weight ratio between the amor-phous active ingredient, the water soluble polymer polyvinylpyrrolidone and the cellulose ether in the first phase is in the range from 1:20:30 to 10:2:1, and the weight ratio between the cellulose ether of the first phase having an average molecular weight in the range of 5000 g/mol to 50000 g/mol and the cellulose ether of the second phase having an average molecular weight in the range of 50000 g/mol to 300000 g/mol is in the range of 5:1 to 1:5;

and a third phase surrounding the core and represented by a coating, said third phase being at film coating consisting of an ester of hydroxypropylmethylcellulose with phthalic anhydride in the weight ratio of the coating with respect to the core ranging from 2 to 10 wt % or of a copolymerizate of methacrylic acid and ethyl acrylate in the weight ratio of the coating with respect to the core in the range from 2 to 15 wt % and usual adjuvants.

2. A three-phase pharmaceutical form according to claim 1, characterized in that the active ingredient is selected from the group consisting of active ingredients acting as analgesics, anticonvulsants, antiparkinsonian drugs, anesthetics, antibiotics, antimalarials, antihypertensives, antihistaminics, antipyretics, alpha-blockers, alpha-adrenergic agonists, bactericides, bronchodilators, beta-adrenergic stimulants, beta-adrenergic blockers, contraceptives, cardiovascular active ingredients, calcium channel inhibitors, diuretics, hypnotics, hormones, hyperglycemics, hypoglycemics, muscle relaxants and contractors, parasympathomimetics, sedatives, sympathomimetics, tranquilizers, antimigraine drugs, and vitamins.

3. A three-phase pharmaceutical form according to claim 1, characterized in that the active ingredient is nifedipine.

4. A three-phase pharmaceutical form according to claim 1, characterized in that the active ingredient is felodipine.

5. A three-phase pharmaceutical form according to claim 1, characterized in that the active ingredient is nicardipine hydrochloride.

6. A three-phase pharmaceutical form according to claim 1, characterized in that the active ingredient is amlodipine benzenesulfonate.

7. A three-phase pharmaceutical form according to claim 1, characterized in that the active ingredient is fenofibrate.

8. A three-phase pharmaceutical form according to claim 1, characterized in that the first phase of the pharmaceutical form contains the water-soluble polymer polyvinylpyrrolidone with an average molecular weight in the range from 2000 g/mol to 1100000 g/mol.

9. A three-phase pharmaceutical form according to claim 1, characterized in that the first phase of the pharmaceutical form contains the water-soluble polymer polyvinylpyrrolidone with a K-value in the range from 10 to 95.

10. A three-phase pharmaceutical form according to claim 1, characterized in that the first phase of the pharmaceutical form contains a surfactant selected from the group consisting of sodium lauryl sulfate, various types of poloxamers, natural or synthetic lecithins and esters of sorbitan with various fatty acids, esters of polyethylene sorbitan with various fatty acids, derivatives of polyoxyethylated castor oil, derivatives of polyoxyethylated hydrogenated castor oil, and esters of polyoxyethylene with various fatty acids.

11. A three-phase pharmaceutical form according to claim 1, characterized in that the first phase of the pharmaceutical form contains a cellulose ether selected from the group consisting of methylcellulose, ethylcellulose, hydroxyethylcellulose, propylcellulose, hydroxypropylcellulose, hydroxypropylmethylcellulose, and carboxymethylcellulose.

12. A three-phase pharmaceutical form according to claim 1, characterized in that the first phase of the pharmaceutical form contains a cellulose ether which is a hydroxypropylmethylcellulose with a content of methoxy groups ranging from 19 to 30% and with a content of hydroxypropoxy groups ranging from 4 to 12%.

13. A three-phase pharmaceutical form according to claim 1, characterized in that the second phase of the pharmaceutical form contains a cellulose ether selected from the group consisting of methylcellulose, ethylcellulose, hydroxyethylcellulose, propylcellulose, hydroxypropylcellulose, hydroxypropylmethylcellulose and, carboxymethylcellulose.

14. A three-phase pharmaceutical form according to claim 1, characterized in that the second phase of the pharmaceutical form contains a cellulose ether which is hydroxypropylmethylcellulose with a content of methoxy groups ranging from 19 to 30% and with content of hydroxypropoxy groups ranging from 4 to 12%.

15. A three-phase pharmaceutical form according to claim 1, characterized in that the second phase of the pharmaceutical form contains a mixture of mono-, di- and triglycerides comprising from 20 to 60 wt. % of triglyceride, from 25 to 65 wt. % of diglyceride, from 10 to 20 wt. % of monoglyceride and from 0 to 5 wt. % of glycerol.

16. A three-phase pharmaceutical form according to claim 1, characterized in that the mixture of mono-, di- and triglycerides is selected from the group consisting of a mixture of glycerol mono-, di- and tristearate, a mixture of glycerol mono-, di- and tripalmitate, a mixture of glycerol mono-, di- and trioleate, and a mixture of glycerol mono-, di- and tripalmitostearate.

17. A three-phase pharmaceutical form according to claim 1, characterized in that the second phase of the pharmaceutical form contains adjuvants selected from the group consisting of lactose, starch, saccharose, gelatin, carboxymethylcellulose, sodium cross-linked carboxymethylcellulose, polyvinylpyrrolidone, cross-linked polyvinylpyrrolidone, magnesium stearate, calcium stearate, aluminum silicate, palmitic acid, stearic acid, and siliconized talc.

18. A three-phase pharmaceutical form according to claim 1, characterized in that the third phase of the pharmaceutical form contains a film coating consisting of an ester of hydroxypropyl methylcellulose with phthalic anhydride with a content of methoxy groups ranging from 18 to 25%, a content of hydroxypropoxy groups ranging from 4 to 10% and content of carboxybenzoyl groups ranging from 20 to 35%.

19. A three-phase pharmaceutical form according to claim 1, characterized in that the third phase of the pharmaceutical form contains a film coating consisting of an ester of hydroxypropyl methylcellulose with phthalic anhydride with an average molecular weight from 2000 g/mol to 100000 g/mol.

20. A three-phase pharmaceutical form according to claim 1, characterized in that the third phase of the pharmaceutical form contains a film coating consisting of a copolymerizate of methacrylic acid and ethyl acrylate with a content of methacrylic groups ranging from 40 to 50%.

21. A three-phase pharmaceutical form according to claim 1, characterized in that the third phase of the pharmaceutical form contains a film coating consisting of a copolymerizate of methacrylic acid and ethyl acrylate with an average molecular weight in the range from 100000 g/mol to 300000 g/mol.

22. A three-phase pharmaceutical form according to claim 1, characterized in that the third phase of the pharmaceutical form contains adjuvants selected from the group consisting of polyethylene glycols of various molecular weights, triacetine, dibutyl sebacate, triethylcitrate, cellulose ethers, additives and pigments.

23. A three-phase pharmaceutical form according to claim 1, characterized in that the weight ratio between the water-soluble polymer polyvinylpyrrolidone and the cellulose ether in the first phase of the three-phase pharmaceutical form is in the range from 1:3 to 3:1.

24. A three-phase pharmaceutical form according to claim 1, characterized in that the weight ratio between the surfactant and the active ingredient is in the range from 0.1:100 to 10:1.

25. A three-phase pharmaceutical form according to claim 1, characterized in that the weight ratio between the surfactant and the active ingredient is in the range from 0.5:100 to 3:1.

26. A three-phase pharmaceutical form according to claim 1, characterized in that the weight ratio between the amorphous active ingredient, the water soluble polymer polyvinylpyrrolidone and the cellulose ether in the first phase of the three-phase pharmaceutical form is in the range from 1:2:3 to 3:2:1.

27. A three-phase pharmaceutical form according to claim 1, characterized in that the weight ratio between the cellulose ether in the first phase and the cellulose ether in the second phase of the three-phase pharmaceutical form is in the range from 3:1 to 1:3.

28. A three-phase pharmaceutical form according to claim 1, characterized in that it is in the form of tablets or capsules.

29. A three-phase pharmaceutical form according to claim 1, wherein the active ingredient is nifedipine in an amount from 30 mg to 90 mg.

30. A three-phase pharmaceutical form according to claim 1, wherein the active ingredient is nifedipine in an amount of 30 mg.

31. A three-phase pharmaceutical form according to claim 1, wherein the active ingredient is nifedipine in an amount of 60 mg.

32. A three-phase pharmaceutical form according to claim 1, wherein the active ingredient is nifedipine in all amount of 90 mg.

33. A process for the preparation of a three-phase pharmaceutical from with constant and controlled release of amorphous active ingredient for a single daily peroral application, containing a core consisting of a first and second phase wherein the first phase contains a mixture of an amorphous active ingredient in an amount from 0.05 mg to 300 mg, the water-soluble polymer polyvinylpyrrolidone in the range from 1 to 40 wt. % with respect to the total weight of the pharmaceutical form, a surfactant in the range from 0.1 to 20 wt % with respect to the total weight of the pharmaceutical form and a cellulose ether in the range from 10 to 70 wt % with respect to the total weight of the pharmaceutical form, said first phase being homogeneously mixed with the second phase containing a cellulose ether in the range from 5 to 40 wt % with respect to the total weight of the pharmaceutical form, a mixture of mono- di- and triglycerides in the range form 0 to 10 wt % with respect to the total weight of the pharmaceutical form and usual adjuvants;

wherein the weight ratio between the water soluble polymer polyvinylpyrrolidone and the cellulose ether in the first phase is in the range from 1:10 to 10:1, the weight ratio between the amorphous active ingredient, the water soluble polymer polyvinylpyrrolidone and the cellulose ether in the first phase is in the range from 1:20:30 to 10:2:1, and the weight ratio between the cellulose ether of the first phase having an average molecular weight in the range of 5000 g/mol to 50000 g/mol and the cellulose ether of the second phase having an average molecular weight in the range of 50000 g/mol to 300000 g/mol is in the range off 5:1 to 1:5 and at third phase surrounding, the core and represented by a coating, said third phase being a film coating consisting of an ester of hydroxypropylmethylcellulose with phthalic anhydride in the weight ratio of the coating with respect to the core ranging from 2 to 10 wt % or of a copolymerizate of methacrylic acid and ethyl acrylate in the weight ratio of the coating with respect to the core in the range from 2 to 15 wt % and usual adjuvants, wherein an active ingredient, a surfactant and the water-soluble polymer polyvinylpyrrolidone are dissolved in an organic solvent at a temperature from 30° C. to 70° C. in a fluid bed granulator the resulting solution is sprayed onto cellulose ether in the fluid bed, the obtained granulate is homogeneously mixed with a cellulose ether and other usual adjuvants at room temperature and the granulate is compressed into tablets, which are coated with at film coating.

34. A process for the preparation of a three-phase pharmaceutical form according to claim 33, characterized in that as the organic solvent the are selected solvents from the group consisting of alcohols, ketones, esters, ethers, aliphatic hydrocarbons, halogenated hydrocarbons, cycloaliphatic, aromatic, heterocyclic solvents and mixtures thereof.

35. A process for the preparation of a three-phase pharmaceutical form according to claim 33, characterized in that as the organic solvent are solvents selected from the group consisting of ethanol, methanol, isopropyl alcohol, n-butyl alcohol, acetone, diethyl ether, ethyl acetate, isopropyl acetate, methyl acetate, dichloromethane, chloroform, and mixtures thereof.

36. A process for the preparation of a three-phase pharmaceutical form according to claim 33, characterized in that the active ingredient is selected from the group consisting of active ingredients acting as analgesics, anticonvulsants, antiparkinsonian drugs, anesthetics, antibiotics, antimalarials, antihypertensives, antihistaminics, antipyretics, alphablockers, alpha-adrenergic agonists, bactericides, bronchodilators, beta-adrenergic stimulants, beta-adrenergic blockers, contraceptives, cardiovascular agents, calcium channel inhibitors, diuretics, hypnotics, hormones, hyperglycemics, hypoglycemics, muscle relaxants and contractors, parasympathomimetics, sedatives, sympathomimetics, tranquilizers, antimigraine drugs, and vitamins.

37. A process for the preparation of a three-phase pharmaceutical form according to claim 33, characterized in that the active ingredient is nifedipine.

38. A process for the preparation of a three-phase pharmaceutical form according to claim 33, characterized in that the active ingredient is felodipine.

39. A process for the preparation of a three-phase pharmaceutical form according to claim 33, characterized in that the active ingredient is nicardipine hydrochloride.

40. A process for the preparation of a three-phase pharmaceutical form according to claim 33, characterized in that the active ingredient is amlodipine benzene sulfonate.

41. A process for the preparation of a three-phase pharmaceutical form according to claim 33, characterized in that the active ingredient is fenofibrate.

42. A process for the preparation of a three-phase pharmaceutical form according to claim 33, characterized in that the first phase of the pharmaceutical form contains the water-soluble polymer polyvinylpyrrolidone with an average molecular weight in the range from 2000 g/mol to 1100000 g/mol.

43. A process for the preparation of a three-phase pharmaceutical form according to claim 32, characterized in that the first phase of the pharmaceutical form contains the water-soluble polymer polyvinylpyrrolidone with a K-value ranging from 10 to 95.

44. A process for the preparation of a three-phase pharmaceutical form according to claim 33, characterized in that the first phase of the pharmaceutical form contains a surfactant selected from the group consisting of sodium lauryl sulfate, various types of poloxamers, natural and synthesized lecithins and esters of sorbitan with various fatty acids, esters of polyoxyethylene sorbitan with various fatty acids, derivatives of polyoxyethylated castor oil, derivatives of polyoxyethylated hydrogenated castor oil, and esters of polyoxyethylene with various fatty acids.

45. A process for the preparation of a three-phase pharmaceutical form according to claim 33, characterized in that the first phase of the pharmaceutical form contains the cellulose ether selected from a group consisting of methylcellulose, ethylcellulose, hydroxyethylcellulose, propylcellulose, hydroxypropylcellulose, hydroxypropylmethylcellulose, and carboxymethylcellulose.

46. A process for the preparation of a three-phase pharmaceutical form according to claim 33, characterized in that the first phase of the pharmaceutical form contains a cellulose ether which is hydroxypropylmethylcellulose with a content of methoxy groups ranging from 19 to 30% and with a content of hydroxypropoxy groups ranging from 4 to 12%.

47. A process for the preparation of a three-phase pharmaceutical form according to claim 33, characterized in that the second phase of the pharmaceutical form contains the cellulose ether selected from a group consisting of methylcellulose, ethylcellulose, hydroxyethylcellulose, propylcellulose, hydroxypropylcellulose, hydroxypropylmethylcellulose, and carboxymethylcellulose.

48. A process for the preparation of a three-phase pharmaceutical form according to claim 33, characterized in that the second phase of the pharmaceutical form contains a cellulose ether with an average molecular weight ranging from 50000 g/mol to 300000 g/mol.

49. A process for the preparation of a three-phase pharmaceutical form according to claim 33, characterized in that the second phase of the pharmaceutical form contains a cellulose ether, which is a hydroxypropylmethylcellulose with a content of methoxy groups ranging from 19 to 30% and with a content of hydroxypropoxy groups ranging from 4 to 12%.

50. A process for the preparation of a three-phase pharmaceutical form according to claim 33, characterized in that the second phase of the pharmaceutical form contains a mixture of mono-, di- and triglycerides comprising from 20 to 60 wt. % of triglyceride, from 25 to 65 wt. % of diglyceride, from 10 to 20 wt. % of monoglyceride and from 0 to 5 wt. % of glycerol.

51. A process for the preparation of a three-phase pharmaceutical form according to claim 33, characterized in that the mixture of mono-, di- and triglycerides is selected from the group consisting of a mixture of glycerol mono-, di- and tristearate, a mixture of glycerol mono-, di- and tripalmitate, a mixture of glycerol mono-, di- and trioleate, and a mixture of glycerol mono-, di- and tripalmitostearate.

52. A process for the preparation of a three-phase pharmaceutical form according to claim 33, characterized in that the second phase of the pharmaceutical form contains adjuvants selected from the group consisting of lactose, starch, saccharose, gelatin, carboxymethylcellulose, sodium cross-linked carboxymethylcellulose, polyvinylpyrrolidone, cross-linked polyvinylpyrrolidone, magnesium stearate, calcium stearate, aluminum silicate, palmitic acid, stearic acid, and siliconized talc.

53. A process for the preparation of a three-phase pharmaceutical form according to claim 33, characterized in that the third phase of the pharmaceutical form contains a film coating consisting of an ester of hydroxypropyl methylcellulose with phthalic acid anhydride with a content of methoxy groups ranging from 18 to 25%, with a content of hydroxypropoxy groups ranging from 4 to 10% and with a content of carboxybenzoyl groups ranging from 20 to 35%.

54. A process for the preparation of a three-phase pharmaceutical form according to claim 33, characterized in that the third phase of the pharmaceutical form contains a film coating consisting of an ester of hydroxypropyl methylcellulose with phthalic anhydride with an average molecular weight from 2000 g/mol to 100000 g/mol.

55. A process for the preparation of a three-phase pharmaceutical form according to claim 33, characterized in that the third phase of the pharmaceutical form contains a film coating consisting of a copolymerizate of methacrylic acid and ethyl acrylate with a content of methacrylic groups ranging from 40 to 50%.

56. A process for the preparation of a three-phase pharmaceutical form according to claim 33, characterized in that the third phase of the pharmaceutical form contains a film coating consisting of a copolymerizate of methacrylic acid and ethyl acrylate with an average molecular weight ranging from 100000 g/mol to 300000 g/mol.

57. A process for the preparation of a three-phase pharmaceutical form according to claim 33, characterized in that the third phase of the pharmaceutical form contains adjuvants selected from the group consisting of polyethylene glycols of various molecular weights, triacetine, dibutyl sebacate triethylcitrate, cellulose ethers, additives, and pigments.

58. A process for the preparation of a three-phase pharmaceutical form according to claim 33, characterized in that the weight ratio between the water-soluble polymer polyvinylpyrrolidone and the cellulose ether in the first phase of the three-phase pharmaceutical form is in the range from 1:3 to 3:1.

59. A process for the preparation of a three-phase pharmaceutical form according to claim 33, characterized in that the weight ratio between the surfactant and the active ingredient is in the range from 0.1:100 to 10:1.

60. A process for the preparation of a three-phase pharmaceutical form according to claim 33, characterized in that the weight ratio between the surfactant and the active ingredient is in the range from 0.5:100 to 3:1.

61. A process for the preparation of a three-phase pharmaceutical form according to claim 33, characterized in that the weight ratio between the amorphous active ingredient, the water-soluble polymer polyvinylpyrrolidone and the cellulose ether in the first phase of the three-phase pharmaceutical form is in the range from 1:2:3 to 3:2:1.

62. A process for the preparation of a three-phase pharmaceutical form according to claim 33, characterized in that the weight ratio between the cellulose ether in the first phase and the cellulose ether in the second phase of the three-phase pharmaceutical form is in the range from 3:1 to 1:3.

63. A process for the preparation of a three-phase pharmaceutical form according to claim 33, characterized in that the three-phase pharmaceutical form is in the form of tablets or capsules.

* * * * *